United States Patent
Pretre et al.

(10) Patent No.: US 9,226,735 B2
(45) Date of Patent: Jan. 5, 2016

(54) ARTICULATING CRANIAL BOLT

(75) Inventors: Isabelle Pretre, Oberdorf (CH); Samuel Leuenberger, Oberdorf (CH); Jens Richter, Oberdorf (CH); Urs Hulliger, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 324 days.

(21) Appl. No.: 13/426,103

(22) Filed: Mar. 21, 2012

(65) Prior Publication Data

US 2013/0072876 A1    Mar. 21, 2013

Related U.S. Application Data

(60) Provisional application No. 61/487,946, filed on May 19, 2011, provisional application No. 61/523,648, filed on Aug. 15, 2011.

(51) Int. Cl.

| A61B 19/00 | (2006.01) |
|---|---|
| A61B 17/00 | (2006.01) |
| A61M 25/04 | (2006.01) |
| A61M 5/32 | (2006.01) |
| A61B 17/34 | (2006.01) |

(52) U.S. Cl.
CPC ......... *A61B 17/00234* (2013.01); *A61B 19/201* (2013.01); *A61M 25/04* (2013.01); *A61B 17/3403* (2013.01); *A61B 2019/208* (2013.01)

(58) Field of Classification Search
CPC ............ A61M 25/04; A61M 39/0247; A61M 2025/0213; A61M 2025/0233; A61M 2025/0286; A61M 25/02; A61M 2025/028; A61M 39/0208; A61B 19/00; A61B 19/201; A61B 2019/208; A61B 17/00234; A61B 17/3403; A61B 17/864

USPC .......... 604/129–130, 175–180, 53, 264, 300; 606/53, 54, 130, 60, 286, 288–191, 606/300, 301, 304
See application file for complete search history.

(56) References Cited

U.S. PATENT DOCUMENTS

| 3,055,370 | A |  | 9/1962 | McKinney et al. |
|---|---|---|---|---|
| 4,809,694 | A |  | 3/1989 | Ferrara |
| 5,257,973 | A | * | 11/1993 | Villasuso ...................... 604/539 |
| 5,634,911 | A |  | 6/1997 | Hermann et al. |

(Continued)

FOREIGN PATENT DOCUMENTS

| EP | 2 168 511 | 3/2010 |
|---|---|---|
| GB | 2469083 | 10/2010 |

(Continued)

*Primary Examiner* — Edelmira Bosques
*Assistant Examiner* — Leah Swanson
(74) *Attorney, Agent, or Firm* — Fay Kaplun & Marcin, LLP

(57) ABSTRACT

A catheter guiding device includes a bolt including a shaft configured to be inserted within a hole drilled in a bone and a passageway extending longitudinally therethrough along a bolt axis and a guide member received within the passageway of the bolt and extending longitudinally along a guide axis. The guide member includes a guide channel extending therethrough along the guide axis, wherein, in a first configuration, the guide member is arrangeable to a desired position relative to the bolt to align the guide axis with a target area and, in a second configuration, the guide member is fixed in the desired position relative to the bolt such that the guide axis is at a desired angle relative to the bolt axis within a permitted range of angulations.

22 Claims, 13 Drawing Sheets

(56) References Cited

U.S. PATENT DOCUMENTS

| | | |
|---|---|---|
| 6,162,196 A | 12/2000 | Hart et al. |
| 6,235,033 B1 | 5/2001 | Brace et al. |
| 7,682,379 B2 | 3/2010 | Mathieu et al. |
| 2003/0040753 A1* | 2/2003 | Daum et al. ............... 606/96 |
| 2004/0167543 A1 | 8/2004 | Mazzocchi et al. |
| 2006/0058797 A1 | 3/2006 | Mathieu et al. |
| 2006/0195104 A1* | 8/2006 | Schlafli et al. ............ 606/72 |
| 2006/0217666 A1 | 9/2006 | Wenchell |
| 2006/0235400 A1 | 10/2006 | Schneider |
| 2009/0326519 A1* | 12/2009 | Wilson et al. ............ 606/1 |
| 2010/0081880 A1* | 4/2010 | Widenhouse et al. ...... 600/201 |

FOREIGN PATENT DOCUMENTS

| | | |
|---|---|---|
| WO | 98/17191 | 4/1998 |
| WO | 01/78814 | 10/2001 |
| WO | 2009/149398 | 12/2009 |

* cited by examiner

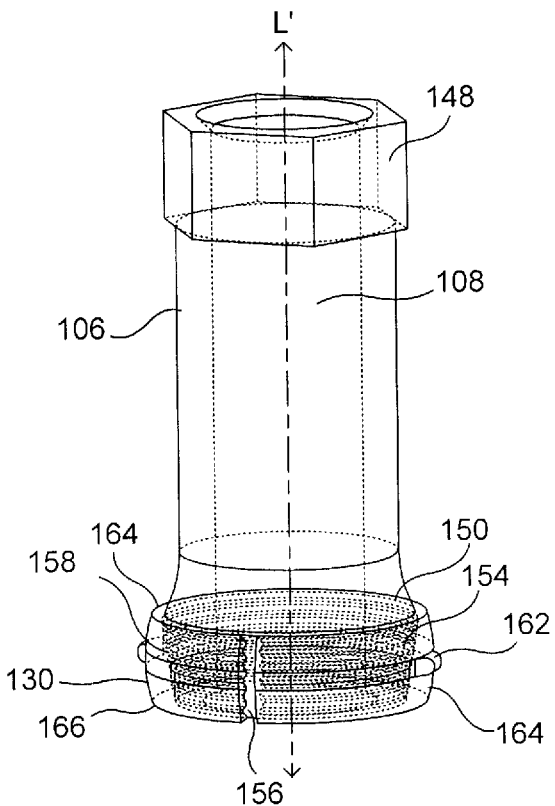
F I G. 9
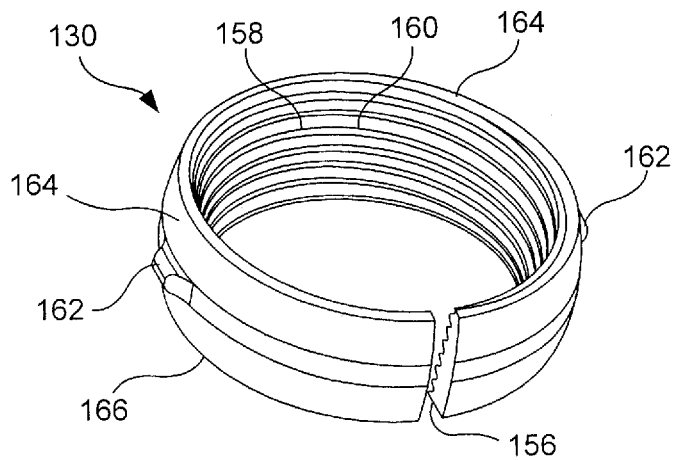
F I G. 10

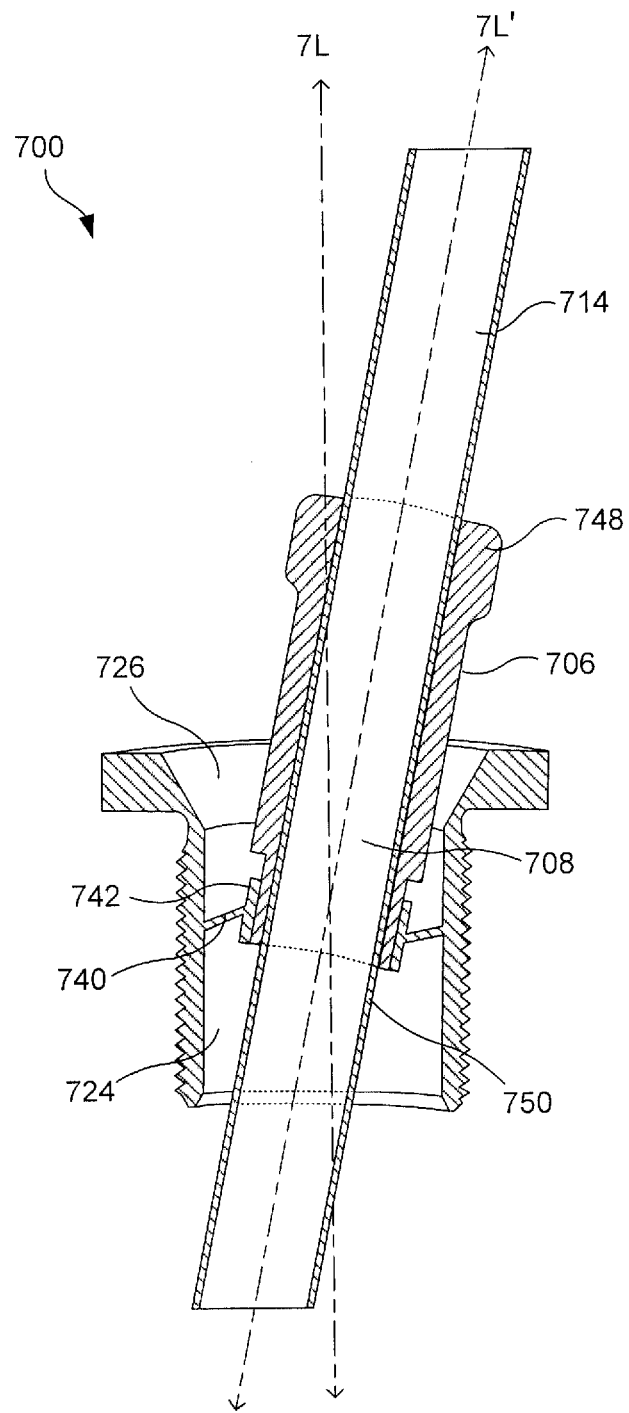
F I G. 23

ARTICULATING CRANIAL BOLT

PRIORITY CLAIM

The present application claims priority to U.S. Provisional Application Ser. No. 61/487,946 filed on May 19, 2011 and entitled "Articulating Multi-Lumen Cranial Bolt" and U.S. Provisional Application Ser. No. 61/523,648 filed on Aug. 15, 2011 and entitled "Articulating Cranial Bolt," the entire disclosures of which are incorporated herein by reference.

FIELD OF THE INVENTION

The present invention relates to the treatment of elevated intracranial pressure (ICP) and, in particular, relates to a system and method for draining cerebrospinal fluid (CSF).

BACKGROUND

Brain trauma or other neurological conditions may cause intracranial pressure (ICP) to rise, resulting in severe harm if it is not treated. For example, an increase in pressure may crush brain tissue, cause the brain to herniate, restrict blood supply to portions of the brain and may, in some cases, be fatal. Elevated ICP may be treated by draining cerebrospinal fluid (CSF) from the ventricles using a drainage catheter. In non-trauma cases, this procedure may be fairly simple as cranial landmarks such as, for example, Kocher's point, are well established for locating the positions of the ventricles. A hole may be drilled through the skull and the catheter inserted therethrough substantially perpendicular to the surface of the skull. In trauma cases, however, the ventricles may be shifted or collapsed making them difficult to locate without using imaging devices or ultrasound. Thus, several holes may need to be drilled into the skull and multiple catheter passes attempted before the ventricles are located.

While some surgeons prefer to secure ICP and drainage catheters via tunneling, a skull bolt may also be used to secure a catheter when additional physiological parameters such as, for example, oxygen, temperature, cerebral blood flow, microdialysis, etc., must be monitored as additional monitoring probes may be inserted through skull bolt. However, sensing zones of these monitoring probes may cross over or contact one another, resulting in artifacts and/or measuring errors.

SUMMARY OF THE INVENTION

The present invention is directed to a catheter guiding device comprising a bolt including a shaft configured to be inserted within a hole drilled in a bone and a passageway extending longitudinally therethrough along a bolt axis and a guide member received within the passageway of the bolt and extending longitudinally along a guide axis, the guide member including a guide channel extending therethrough along the guide axis, wherein, in a first configuration, the guide member is arrangeable to a desired position relative to the bolt to align the guide axis with a target area and, in a second configuration, the guide member is fixed in the desired position relative to the bolt such that the guide axis is at a desired angle relative to the bolt axis within a permitted range of angulations.

BRIEF DESCRIPTION OF THE DRAWINGS

FIG. 9 shows a perspective view of a guide member and a bushing of the catheter guiding device of FIG. 3;

FIG. 10 shows the bushing of the catheter guiding device of FIG. 3;

FIG. 23 shows a cross-sectional side view of the system of FIG. 22;

DETAILED DESCRIPTION

Figure 1:
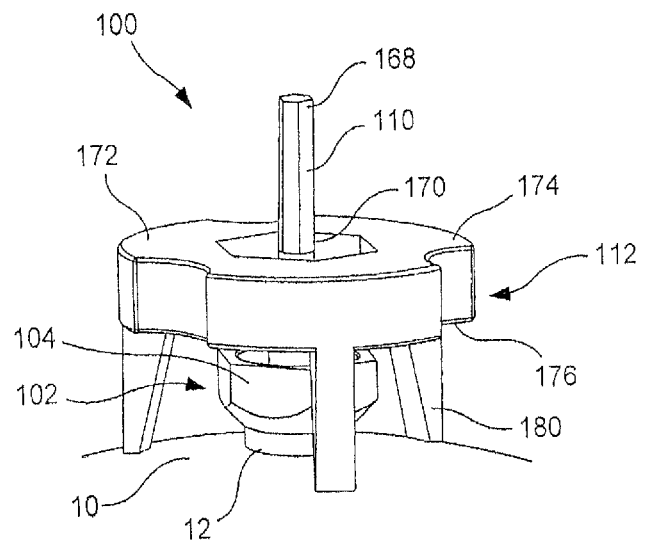
FIG. 1 shows a perspective view of a system according to a first exemplary embodiment of the present invention.

The present invention may be further understood with reference to the following description and the appended drawings, wherein like elements are referred to with the same reference numerals. The present invention relates to the treatment of elevated intracranial pressure (ICP) and, in particular, relates to a system and method for draining cerebrospinal fluid (CSF). Exemplary embodiments of the present invention describe a catheter guiding device including a skull bolt and a guide member movable relative thereto such that a drainage catheter may be inserted through the guide member to a target location via a single hole drilled in the skull into which the bolt is inserted. It will be understood by those of skill in the art that although the exemplary embodiments specifically describe a device for insertion of a catheter through a hole drilled in the skull, the device of the present invention may be used for any bone through which it is desirable to pass a catheter or other similar device. It should be noted that the terms "proximal" and "distal" as used herein, are intended to refer to a direction toward (proximal) and away from (distal) a surgeon or other user of the device.

Figure 2:
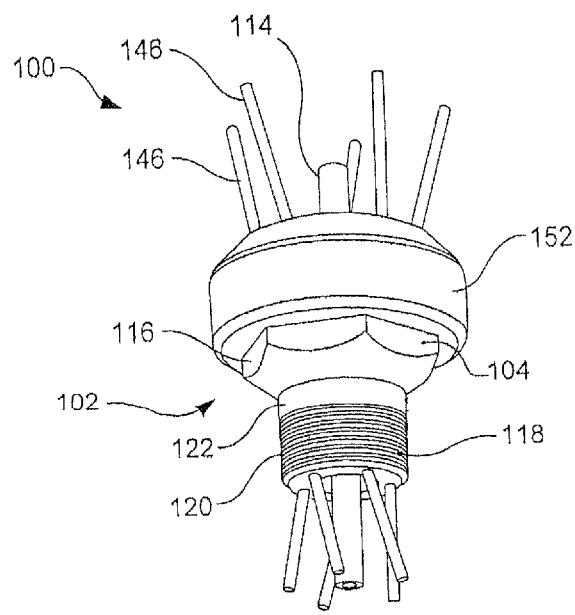
FIG. 2 shows another perspective view of the system of FIG. 1.
Figure 3:
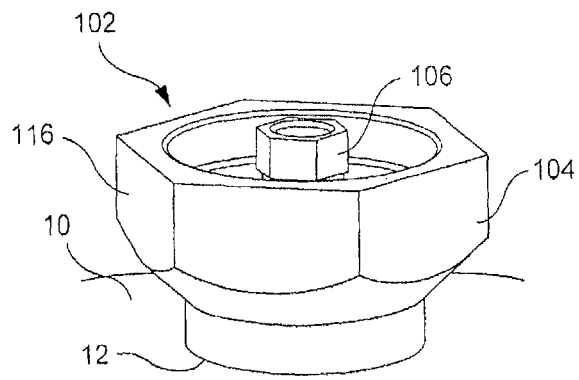
FIG. 3 shows a perspective view of the catheter guiding device of the system of FIG. 1.

As shown in FIGS. 1-12, a system 100 comprises a catheter guiding device 102 including a hollow bolt 104 sized and shaped for insertion into a hole 12 drilled in the skull 10 and a guide member 106 movably coupled thereto via a bushing 130. The guide member 106 includes a guide channel 108 extending therethrough for receiving a drainage catheter 114 therein, as shown in FIG. 1. The guide member 106 may be angled with respect to the bolt 104 such that the catheter 114 may be inserted through the guide channel 108 along a path directed to a target location (i.e., a ventricle from which CSF is to be drained) via the hole 12 in the skull 10 into which the bolt 104 has been inserted. The catheter guide device 102 may further include peripheral channels 144 extending through the bolt 104 configured such that monitoring probes 146 for monitoring parameters such as, for example, oxygen, temperature, microdialysis, etc., may be inserted through the single hole 12 drilled in the skull 10 without intersecting one another and/or the catheter 114. As would be understood by those skilled in the art, the system 100 may also further comprise a sealing cap 152 couplable to a head portion 116 of the bolt 104 for sealing the proximal end of the bolt 104 when the passages extending therethrough are not in use. As shown in FIG. 2, the system 100 may further comprise a driving element 110 for fixing the guide member 106 in a desired position relative to the bolt 104 and a tripod 112 which may be used, when desired, to position the channel 108 substantially perpendicular to a surface of the skull.

As shown in FIGS. 3-8, the bolt 104 includes a head portion 116 and a shaft 118 extending distally therefrom. The shaft 118 may include a threading 120 extending along a portion of an outer surface 122 thereof for engaging the bony surface of the skull 10 surrounding the hole 12. The head portion 116 according to this embodiment is sized and shaped to engage a driving tool which may be used to drive (e.g. rotate) the bolt 104 into the hole in the skull. As the skilled person would understand, the head portion 116 may be formed in a particular size and shape. For example, the head portion 116 may be a hexagonal shape for engaging a hexagonally shaped portion of a driving tool. In another example (not shown), the head portion may have two wings, similar to a wingnut, that allow a user to drive the bolt 104 into a hole in the skull by hand. A central channel 124 extends longitudinally through the bolt 104 through both the head portion 116 and the shaft 118 to accommodate the catheter 114 therein. The central channel 124 includes a proximal portion 126 and a distal portion 128. The proximal portion 126 tapers radially inward from a proximal end 132 to a distal end 134 thereof while the distal portion 128 flares radially outward from a proximal end 136 to a distal end 138 thereof. The proximal and distal portions 126, 128 are angled with respect to a longitudinal axis L of the bolt 104 to accommodate the guide member 106, and the catheter 114 inserted through the guide member 106, when the guide member 106 is angled relative to the longitudinal axis L of the bolt 104. The proximal and distal portions 126, 128 may be, for example, angled at approximately 30° relative to the longitudinal axis L such that the guide member 106 may be angled up to approximately 30° with respect to the bolt 104.

The channel 124 may also include a mid-portion 140, which extends between the proximal and distal portions 126, 128 immediately distal of the proximal portion 126 and sized and shaped to receive the bushing 130. A surface of the mid-portion 140 may be substantially concave such that the bushing 130 received therein is permitted to move therewithin. The mid-portion 140 may also include a shoulder 184 extending radially inward to prevent the bushing 130 from moving distally therebeyond and recess 142 extending along a length thereof to receive a projection 162 of the bushing 130 such that the bushing 130 is prevented from rotating relative to the bolt 104. It will be understood by those of skill in the art that the mid-portion 142 may include more than one recess 142. For example, the mid-portion 142 may include two diametrically opposed recesses 142 extending therealong corresponding in position to two diametrically opposed projections 162.

The bolt 104 may further include a plurality of peripheral channels 144 extending therethrough radially outside and distributed circumferentially about the central channel 124. As would be understood by those skilled in the art, the peripheral channels 144 are preferably sized and shaped to accommodate items to be inserted therethrough. For example, one of the channels 144 may be sized and shaped to slidably receive a monitoring probe 146 monitoring a parameter such as, for example, oxygen, temperature, microdialysis, etc. while the other channels 144 may be the same or differently sized and shaped depending on the requirements of the devices to be inserted therethrough. Each of the peripheral channels 144 is separated from the central channel 124 and extends through the bolt 104 at an angle selected to prevent intersection with the catheter 114 and with devices inserted through the other channels 144. A bolt 104 according to this exemplary embodiment includes five peripheral channels 144 equidistantly spaced from one another with each of the channels 144 extending through the bolt 104 at an angle of approximately 15° relative to an axis extending through the bolt 104 parallel to a longitudinal axis of the bolt 104. When a catheter 114 is inserted through the guide member 106 at an angle of 15° with respect to the longitudinal axis L, however, as will be understood by those of skill in the art, one of the peripheral channels 144 may be occluded and may thus not be available for use. It will also be understood by those of skill in the art that the bolt 104 may include any number of peripheral channels 144 at any of a variety of angles.

As shown in FIG. 9, the guide member 106 extends along a longitudinal axis L' from a proximal end 148 to a distal end 150 and includes a guide channel 108 extending therethrough. The guide channel 108 according to this embodiment is sized and shaped for receiving a catheter 114 therethrough. The proximal end 148 is sized and shaped to correspond to a distal end of the driving element 110 such that the driving element 110 may engage the proximal end 148 to exert a driving (e.g., rotative) force thereon. The proximal end 148 may, for example, be hexagonally shaped to be received within a hexagonally shaped distal end of the driving element 110. The distal end 150 may be tapered and include a threading 154 along an outer surface thereof.

Figure 5:
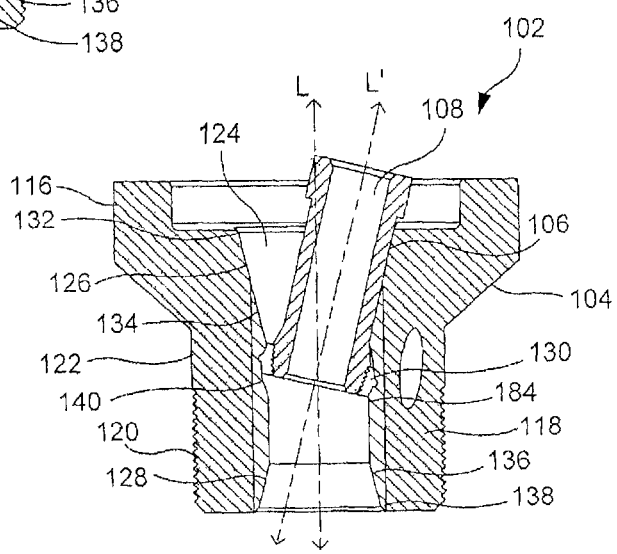
FIG. 5 shows a longitudinal cross-sectional view of the catheter guiding device of FIG. 3, in a second position.
Figure 6:
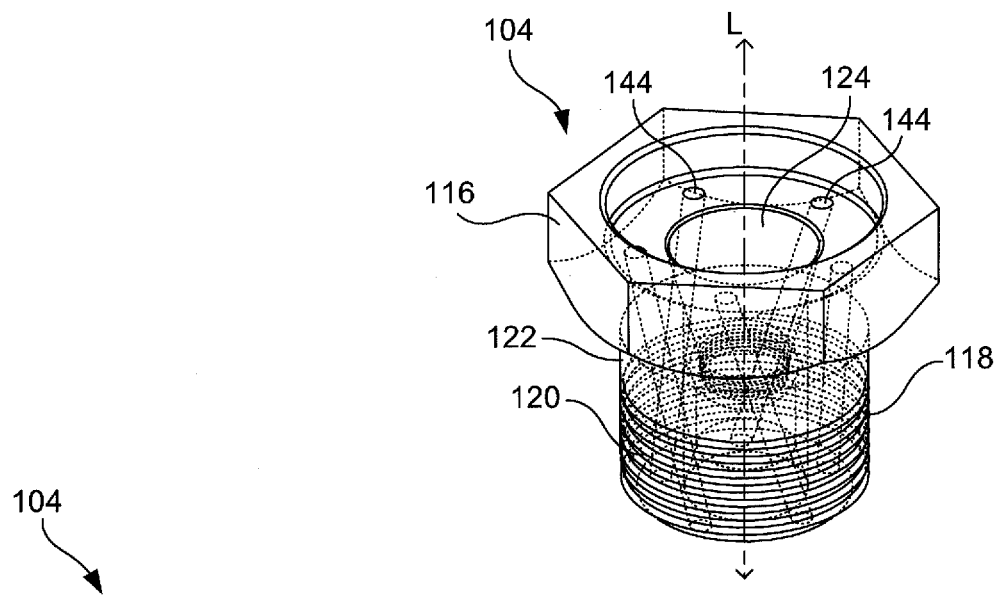
FIG. 6 shows a perspective view of a bolt of the catheter guiding device of FIG. 3.
Figure 7:
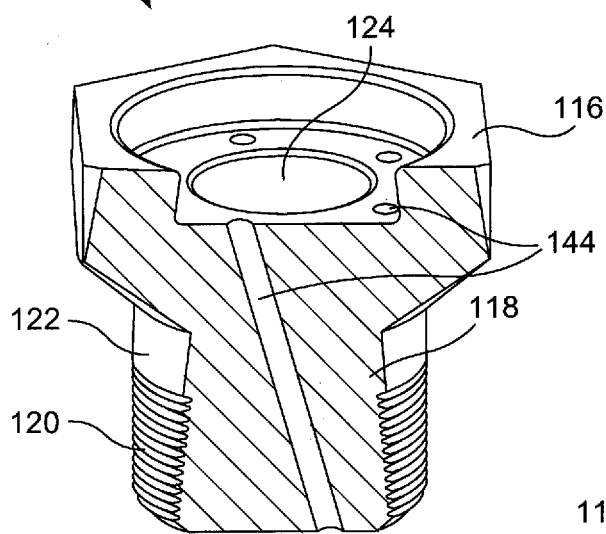
FIG. 7 shows a partially cross-sectional perspective view of the bolt of FIG. 6.
Figure 8:
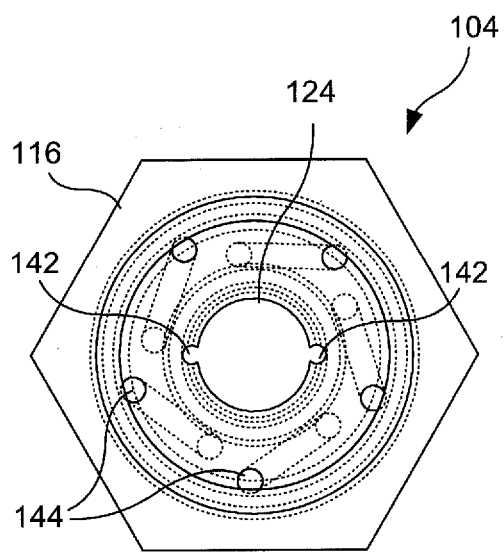
FIG. 8 shows a top plan view of the bolt of FIG. 6.

The guide member 106 is coupled to the bolt 104 via the bushing 130. The bushing 130, as shown in FIG. 10, includes a slot 156 extending therethrough such that the bushing 130 is movable between a non-expanded configuration in which the bushing 130 may be moved relative to the bolt 104 and an expanded configuration in which an outer surface 164 of the bushing 130 engages the mid-portion 140 to fix the bushing 130 in a desired position within the channel 124 of the bolt 104. The bushing 130 includes a protrusion 162 extending from the outer surface 164 thereof to be received within the recess 142. The bushing 130 may include any number of protrusions 162 so long as a number and position of the protrusions 162 corresponds to a number and position the recesses 142. For example, in a preferred embodiment, the bushing 130 may include two diametrically opposed protrusions 162 corresponding to two diametrically opposed recesses 142. The outer surface 164 of the bushing 130 may be partially spherical such that the bushing 130 is movable within the mid-portion 140 of the channel 124. The bushing 130 has an inner surface 158 which tapers from a proximal end 164 to a distal end 166 thereof and includes a threading 160 corresponding to the distal end 150 of the guide member 106. Thus, the bolt 104 and the guide member 106 are coupled by inserting the bushing 130 into the channel 124 and inserting the distal end 150 of the guide member 106 into the bushing 130. The guide member 106 may be moved relative to the bolt 104 such that the longitudinal axis L' of the guide member 106 is angled with respect to the longitudinal axis L up to, for example, an angle of about 30°, as shown in FIG. 5. The protrusion 162 is movable only along a length of the recess 142 so that the bushing 130 and guide member 106 may be angled with respect to the bolt 104 but are prevented from rotating about an axis thereof relative to the bolt 104. Once the guide member 106 has been moved to a desired angle relative to the bolt 104, the guide member 106 may be rotated about the longitudinal axis L' to move the guide member distally relative to the bushing 130 such that the tapered distal end 150 interfaces with the tapered inner surface 158 of the bushing 130 to move the bushing 130 to the expanded configuration, locking the guide member 106 relative to the bolt 104. In one exemplary embodiment, a length of the guide member 106 is selected so that, once the guide member 106 has been fixed in a desired position relative to the bolt 104, the proximal end 148 of the guide member 106 does not extend proximally beyond a proximal surface of the head portion 116 so that the sealing cap 152 may be mounted thereover.

The guide member 106 may be rotated relative to the bushing 130 using the driving element 110, which extends longitudinally from a proximal end 168 to a distal end 170. The distal end 170 is sized and shaped to engage the proximal end 148 of the guide member 106. For example, the distal end 170 of the driving element 110 may include a hexagonal recess for engaging a hexagonally shaped proximal end 148 of the guide member 106. It will be understood by those of skill in the art, however, that the distal end 170 of the driving element 110 may have any of a variety of configurations so long as the distal end 170 engages the guide member 106 such that the guide member 106 may be rotated via rotation of the driving element 110.

Figure 11:
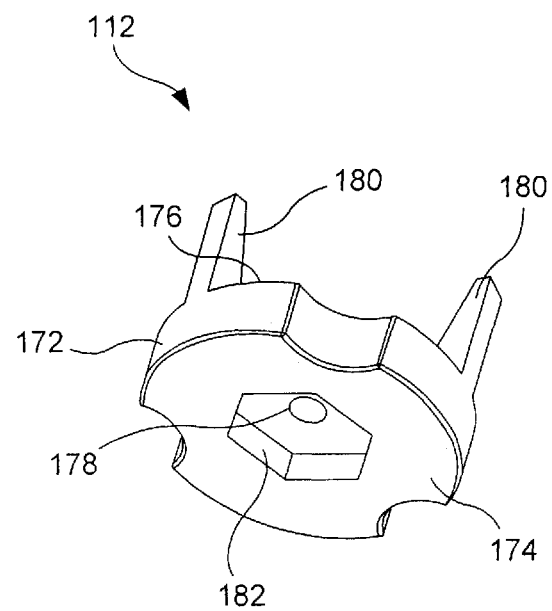
FIG. 11 shows a perspective view of a tripod according to the system of FIG. 1.
Figure 12:
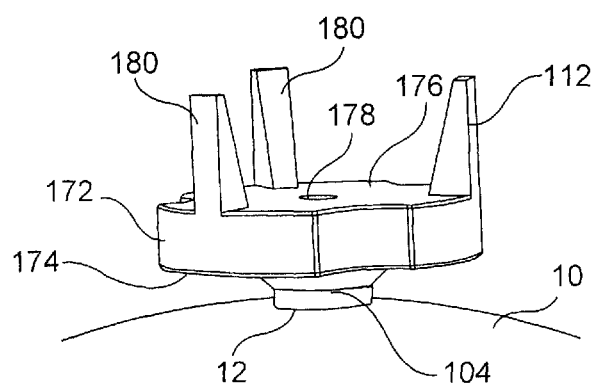
FIG. 12 shows another perspective view of the tripod according to the system of FIG. 1.

As shown in FIGS. 11-12, the tripod 112 comprises a body 172 and legs 180 extending therefrom. The body 172 includes a first surface 174 and a second surface 176 with an opening 178 extending therethrough from the first surface 174 to the second surface 176. The tripod 112 includes three legs 180 which, in this embodiment are of equal lengths, each of which extends from the second surface 176 equidistantly from one another and perpendicularly to the first and second surfaces 174, 176 such that when the tripod 112 is used in a first operative configuration, as shown in FIG. 1, to position the guide member 106 substantially perpendicularly relative to a surface of the skull, the first surface 174 faces away from the skull while the second surface 176 faces toward the skull with the legs 180 resting on the surface thereof. The opening 178 extends through the center of the body 172 along an axis perpendicular to the first and second surfaces 174, 176. The opening 178 is sized and shaped to accommodate the locking element 110 therethrough and shaped to permit the locking element 110 to be rotated relative thereto without causing rotation of the tripod 112. For example, the opening 178 may be substantially circular. Thus, when the locking element 110 is passed through the opening 178, the locking element 110 and the guide member 106 coupled to the distal end 170 are positioned perpendicular to the surface of the skull 10 substantially coaxial with the longitudinal axis L of the bolt 104. The locking element 110 may be rotated relative to the tripod 112 to rotate the guide member 106, moving the guide member 106 distally relative to the bushing 130 such that the bushing 130 expands to lock the guide member 106 relative to the bolt 104.

The tripod 112 may also include a recess 182 along the first surface 174 of the body 102, sized and shaped to correspond to the head portion 116 of the bolt 104. For example, where the head portion 116 of the bolt 104 is hexagonal, the recess 182 may be correspondingly hexagonal. Thus, the tripod 112 may be used in a second operative configuration, as shown in FIG. 12, to tighten the bolt 104 in the hole drilled in the skull. In the second configuration, the tripod 112 is placed over the bolt 104 such that the head portion 116 is received within the recess 182 and the first surface 174 faces the skull 10. The tripod 112 may then be rotated to rotate the bolt 104 about the longitudinal axis L, permitting the threads 120 along the shaft 118 of the bolt 104 to engage the hole in the skull 10.

Figure 4:
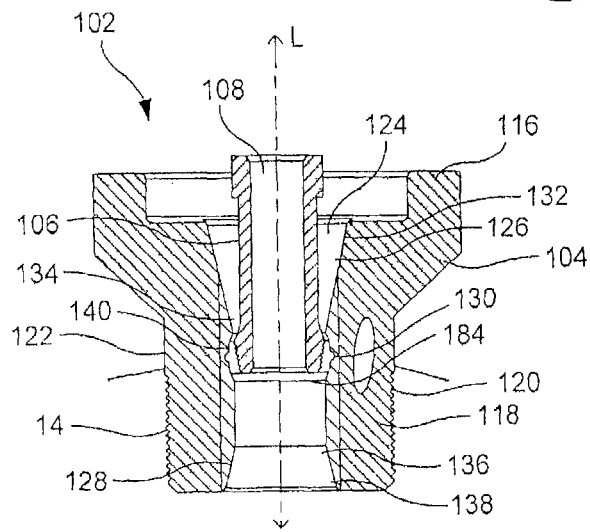
FIG. 4 shows a longitudinal cross-sectional view of the catheter guiding device of FIG. 3, in a first position.

An exemplary surgical technique using the system 100, involves drilling a hole 12 in the skull 10, for example, using well established cranial landmarks for identifying an anatomical location of a target ventricle or using any other known technique. For example, it is known that a ventricle is aligned with an axis perpendicular to the surface of the skull 10 intersecting with Kocher's point. The hole 12 may thus be drilled in the skull 10 at Kocher's point, perpendicular to the surface of the skull 10. The bolt 104 may then be inserted into the hole 12 such that the threading 120 along the shaft 118 engages an inner surface 14 of the hole 12, as shown in FIG. 4. The tripod 112 may be used to further tighten the bolt 104 in the hole 12. In particular, the tripod 112 may be placed over the head portion 116, as shown in FIG. 12, such that the head portion 116 is received within the recess 182 so that the tripod 112 may be rotated to correspondingly rotate the bolt 104 about the longitudinal axis L.

Once the bolt 104 has been inserted as desired, the catheter guiding device 102 is assembled by inserting the bushing 130 into the channel 124 with the protrusion 162 thereof slid into the recess 142 and inserting the distal end 150 of the guide member 106 into the bushing 130. Alternatively, the catheter guiding device 102 may be assembled prior to insertion of the bolt 104 into the hole 12. When the ICP is not a result of brain trauma, the ventricles are most likely located along a central axis of the hole 12. In such cases, as shown in FIG. 1, the tripod 112 may be used to position the longitudinal axis L' of the guide member 106 perpendicular to the surface of the skull 10 and/or substantially coaxial with the longitudinal axis L of the bolt 104, as shown in FIG. 4. The distal end 170 of the driving element 110 is coupled to the proximal end 148 of the guide member 106. The locking element 110 is received within the opening 178 and the tripod 112 is slid thereover until the legs 180 contact the surface of the skull 10. As described above, the configuration of the legs 180 and the opening 178 ensures that the guide member 106 is substantially perpendicular to the surface of the skull 10 when the legs 180 come into contact therewith. Thus, once the legs 180 contact the surface of the skull 10, the driving element 110 may be rotated within the opening 178 to rotate the guide member 106 and move it distally relative to the bushing 130. The bushing 130 thereby expands, locking the guide member 106 in the desired position relative to the bolt 104. Once the guide member 106 has been locked relative to the bolt 104, the tripod 112 and the driving element 110 may be removed from the catheter guiding device 102.

Alternatively, in cases in which the ICP is a result of brain trauma, the ventricles may have shifted or collapsed such that the surgeon or other user must locate the ventricles manually. In these cases, the guide member 106 may need to be angled with respect to the bolt 104 permitting the surgeon to access the ventricles via other paths not coincident with the longitudinal axis of the bolt 104 without drilling any additional hole(s) in the skull 10. Thus, the guide member 106 may be moved such that the longitudinal axis L' is angled with respect to the longitudinal axis L, as shown in FIG. 5, and corresponds to the target location (i.e., the location of the ventricles). Once the surgeon has determined a desired position of the guide member 106 with respect to the bolt 104, the driving element 110 may be coupled to the proximal end 148 of the guide member 106 to rotate the guide member 106 about the longitudinal axis L', locking the guide member 106 in the desired position relative to the bolt 104. The driving element 110 may then be removed from the guide member 106.

Once the guide member 106 has been fixed in the desired position relative to the bolt 104, the catheter 114 is slid through the channel 108 of the guide member 106 and inserted to the target location. Monitoring probes 146 may additionally be inserted through the peripheral channels 144 of the bolt 104. If the longitudinal axis L' is angled with respect to the longitudinal axis L, it will be understood that one of the peripheral channels 144 may intersect with the catheter 114 such that this channel 144 may not be available for the insertion of a monitoring probe 146 therethrough. Upon insertion of the catheter 114 and the desired monitoring probes 146, the cap 152 may be placed over the head portion 116 of the bolt 104 and fastened thereto to hold the probes 146 in place within the channels 144. In one embodiment, the cap 152 is formed of silicone and press fit onto the head portion 116 of the bolt 104. In another embodiment, the cap 152 is snap fit over a rim extending about the head portion 116 of the bolt 104. It will be understood by those of skill in the art, however, that the cap 152 may be coupled to the head portion 116 in any of a variety of different ways. After a desired amount of CSF has been drained and/or the monitoring of any parameters has been completed, the catheter 114 and the monitoring probes 146 are removed from the catheter guiding device 102. The catheter guiding device 102 may then be removed from the skull by disengaging the bolt 104 therefrom via, for example, rotating the bolt 104 such that the threading 120 is disengaged from the hole 112.

Figure 13:
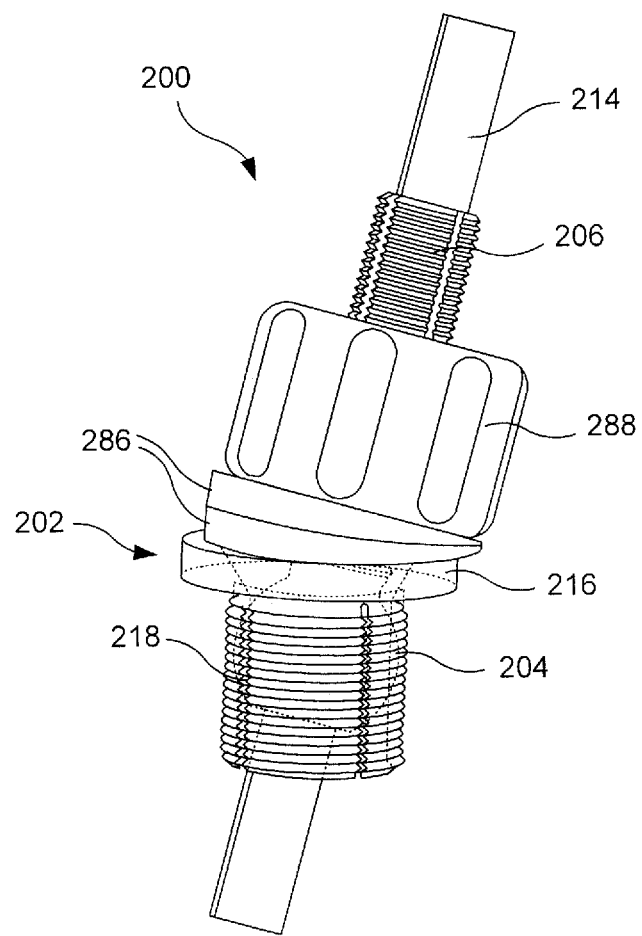
FIG. 13 shows a perspective view of a system according to a second exemplary embodiment of the present invention.
Figure 14:
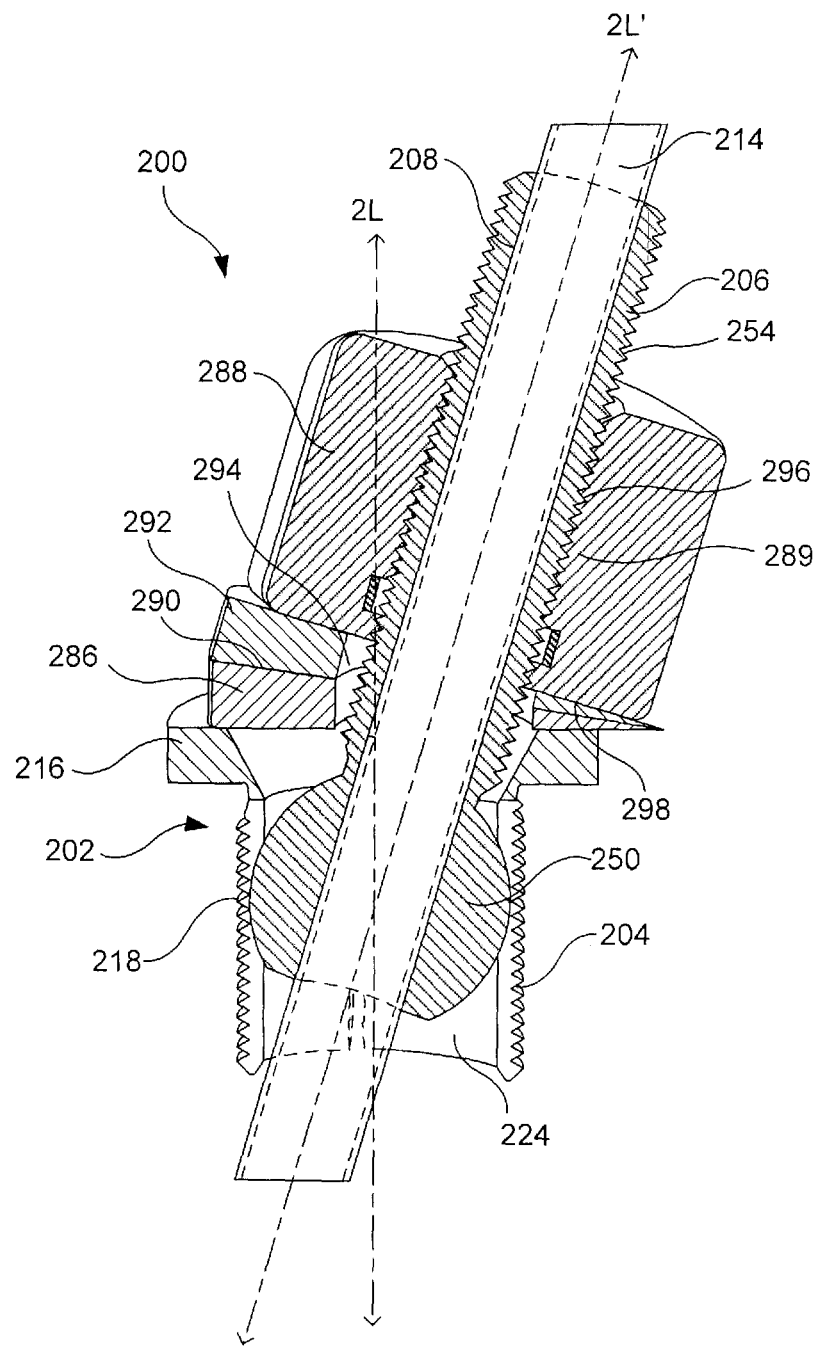
FIG. 14 shows a cross-sectional perspective view of the system of FIG. 13.

As shown in FIGS. 13-14, a system 200 according to a second exemplary embodiment is substantially similar to the system 100, comprising a catheter guiding device 202 including a bolt 204 for engaging a hole drilled in a skull and a guide member 206 movably coupled thereto such that a catheter 214 may be inserted through a guide channel 208 thereof at an angle with respect to a longitudinal axis of the bolt 204. The bolt 204 may be substantially similar to the bolt 104, including a head portion 216, a threaded shaft 218 and a central channel 224 extending therethrough. The guide member 206, however, is coupled to the bolt 204 via a substantially spherically shaped distal end 250 received within the channel 224 to permit the guide member 206 to be pivoted with respect to a longitudinal axis 2L of the bolt 204. The system 200 also comprises a plurality of rings 286 which may be used to pivot the guide member 206 to a desired configuration along with a locking nut 288 thereover for locking the guide member 206 in a desired position relative to the bolt 204.

The rings 286 may be slid over a length of the guide member 206 until the rings 286 rest on the head portion 216 of the bolt 204. The rings 286 include a first surface 290 which, when in an operative position, faces the bolt 204 and a second surface 292 which, when in the operative position, faces away from the bolt 204. An opening 294 extends through the ring 286 from the first surface 290 to the second surface 292. The first and second surfaces 290, 292 are angled with respect to one another. The nut 288 includes an opening 296 extending therethrough, the opening extending substantially perpendicularly to a first surface 298 thereof, which, when the nut 288 is in the operative position, faces the bolt 204 and comes into contact with the second surface 292 of a proximal-most ring 286. The nut 288 includes a threading 289 along a surface of the opening 296 to engage a threading 254 along a length of the guide member 206 such that the nut 288 is threaded over the guide member 206. Thus when the first surface 298 of the nut 288 comes into contact with the proximal-most ring 286, a longitudinal axis 2L' of the guide member 206 which extends therethrough is angled with respect to the longitudinal axis 2L of the bolt 204. In one exemplary embodiment, the system 200 includes two rings 286. It will be understood by those of skill in the art, however, that any number of rings 286 may be utilized to achieve a desired angle. For example, when a single ring 286 is utilized, the longitudinal axis 2L' of the guide member 206 is at a fixed angle relative to the longitudinal axis 2L of the bolt 204. If, however, two or more rings 286 are utilized, the angle between the longitudinal axes 2L, 2L' may be varied as the rings 286 may be rotated thereabout to change an angle and orientation of the guide member 206. Once the desired angle and orientation of the guide member 206 have been achieved, the nut 288 is tightened (i.e., rotated relative to the guide member 206 and moved distally therealong) to fix the guide member 206 in the desired position relative to the bolt 204.

Figure 15:
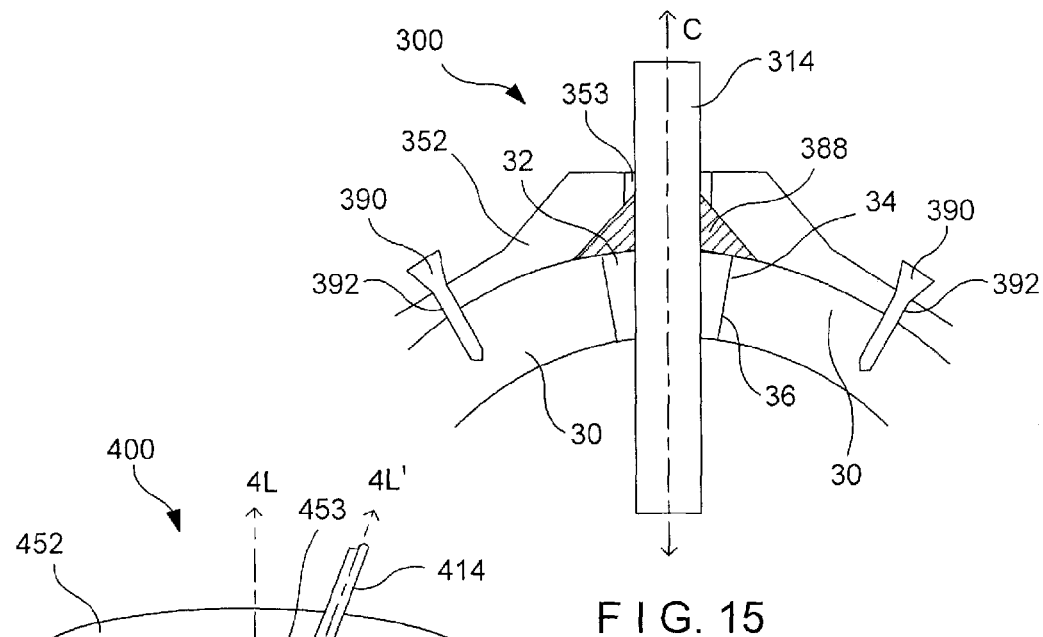
FIG. 15 shows a cross-sectional side view of a system according to a third exemplary embodiment of the present invention.

As shown in FIG. 15, a system 300 according to a third exemplary embodiment of the present invention, comprises a cap 352 which may be slid over a catheter 314 to fix the catheter 314 at a desired angle relative to a central axis C of a hole 32 drilled in a skull 30. In this embodiment, the hole 32 extends along the central axis C and may be substantially conical, tapering from a proximal end 34 to a distal end 36 to accommodate an angulation of the catheter 314 with respect to the central axis C. The catheter 314 may be inserted into the hole 32 and angled with respect to the central axis C, as desired. Once the catheter 314 has been positioned as desired, the cap 352 may be slid thereover. The cap 352 includes an opening 353 extending therethrough and is sized and shaped to accommodate the catheter 314. The cap 352 further includes a soft compressible ring 388 within the opening 352 which receives the catheter 314 therein to seal the hole 32 and prevent axial displacement of the catheter 314. Thus, when the cap 352 is slid over the catheter 314 and fixed to the skull 30, the catheter 314 is maintained in the desired orientation and angle with respect to the central axis C of the hole 32. The cap 352 may be fixed to the skull 30 using, for example, screws 390 inserted through fixation openings 392 of the cap 352. In a preferred embodiment, three screws will be used to fix the cap 352 to the skull 30.

Figure 16:
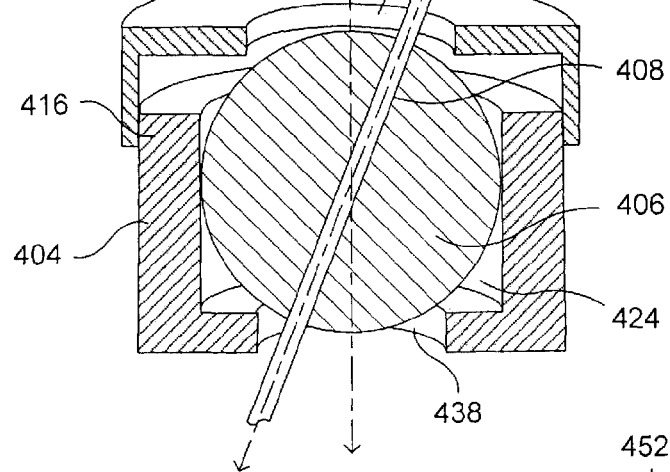
FIG. 16 shows a partial-cross-sectional view of a system according to a fourth exemplary embodiment of the present invention, in a first configuration.
Figure 17:
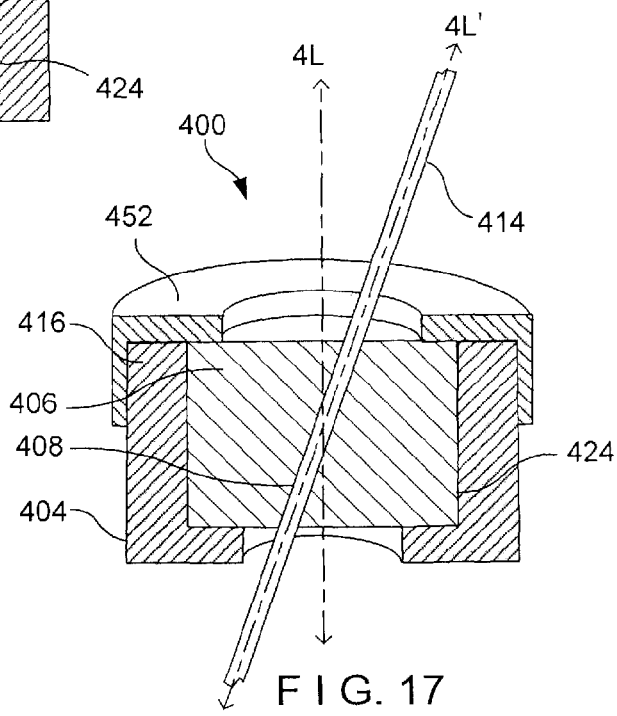
FIG. 17 shows a partial cross-sectional view of the system of FIG. 16, in a second configuration.

As shown in FIGS. 16-17, a system 400 according to a fourth exemplary embodiment of the present invention comprises a bolt 404 for engaging a hole drilled in a skull, a compressible guide member 406 received within a channel 424 of the bolt 404 and a cap 452 which engages the bolt 404 to move the compressible guide member 406 between a non-compressed configuration, as shown in FIG. 16, and a compressed configuration, as shown in FIG. 17. The bolt 404 may be substantially similar to the bolt 104, described above. A distal end 438 of the channel 424 is sized and shaped to prevent the compressible guide member 406 from extending distally therepast. A proximal end 416 of the bolt 404 is configured to engage the cap 452, which includes an opening 453 permitting a catheter 414 to pass therethrough while also preventing the compressible guide member 406 from extending proximally therepast. The proximal end 416 of the bolt 404 may include, for example, a threading extending about an exterior surface thereof. The cap 452 may include a corresponding threading along an interior surface thereof for engaging the threading of the bolt 404. Thus, the cap 452 may be rotated relative to the bolt 404 to move the cap 452 distally relative to the bolt 404. Moving the cap 452 distally relative to the bolt 404 moves the compressible guide member 406 from the non-compressed configuration to the compressed configuration. In another embodiment, the cap 452 may be press fit over the proximal end 416 of the bolt 404. It will be understood by those of skill in the art, however, that the cap 452 may be coupled to the proximal end 416 of the bolt 404 in any of a number of different ways so long as the cap 452 is movable over the proximal end 416 of the bolt 404 to compress the guide member 406.

The compressible guide member 406 is received within the channel 424 and housed therein via the cap 452 which engages the proximal end 416 of the bolt 404. The compressible guide member 406 may be formed of silicone and, in the non-compressed configuration, may be ball-shaped. The guide member 406 includes a channel 408 extending therethrough, which is sized and shaped to receive a catheter 414 therein. In the non-compressed configuration, as shown in FIG. 16, the cap 452 does not come into contact with the guide member 406 such that the ball shape of the guide member 406 permits the guide member 406 to be rotated and/or pivoted relative to a longitudinal axis 4L of the bolt 404. The catheter 414 may be inserted into the channel 408 and moved as desired until a longitudinal axis 4L' of the catheter 414 is at a desired angle with respect to the longitudinal axis 4L. Once the catheter 414 is at the desired angle, the guide member 406 may be compressed, as shown in FIG. 17, by moving the cap distally relative to the bolt 404 such that the cap 452 presses against the guide member 406, causing the guide member 406 to expand radially outward to engage a surface of the channel 424 and radially inward to engage an exterior surface of the catheter 414, thereby fixing the catheter 414 in the desired configuration relative to the bolt 404.

Figure 18:
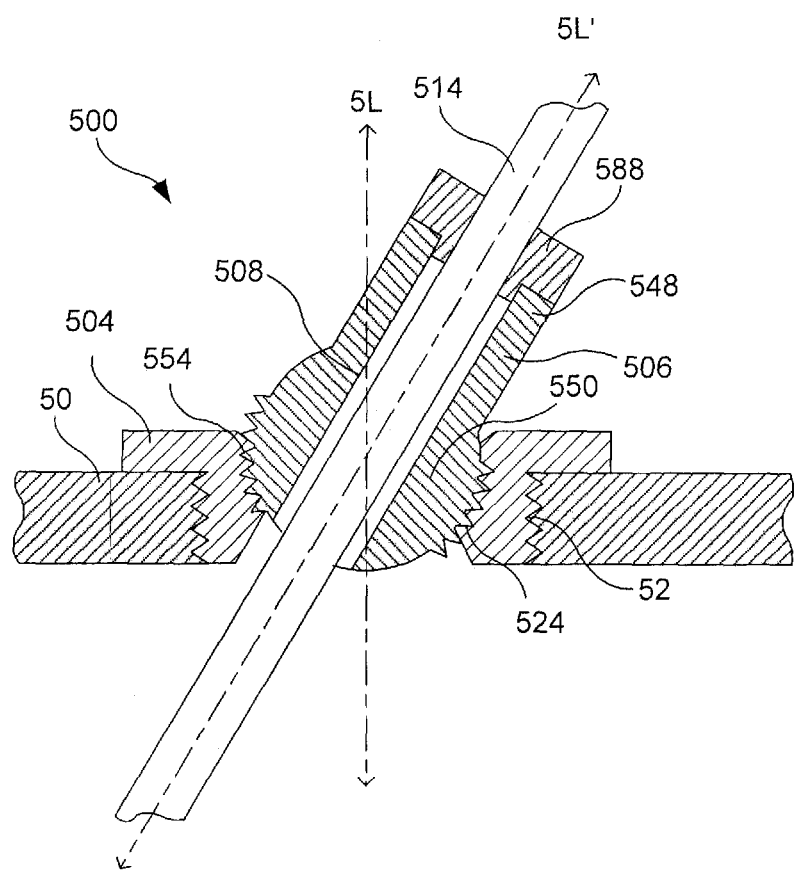
FIG. 18 shows a cross-sectional side view of a system according to a fifth exemplary embodiment of the present invention.
Figure 19:
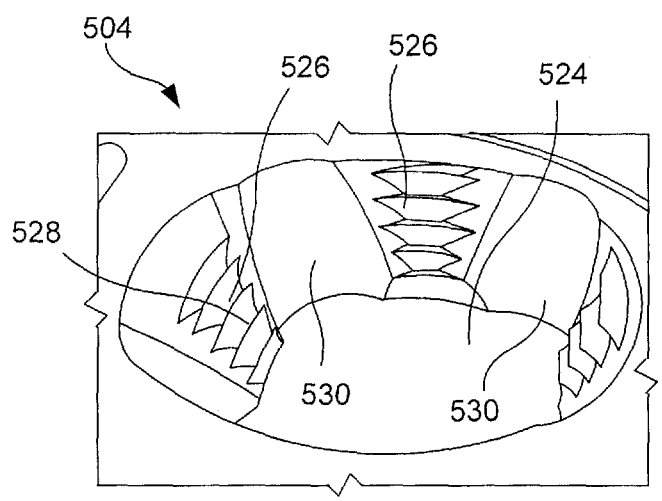
FIG. 19 shows a perspective view of a bolt of the system of FIG. 18.

As shown in FIGS. 18-19, a system 500 according to a fifth exemplary embodiment of the present invention may be substantially similar to the system 100 described above, comprising a bolt 504 for engaging a hole 52 drilled in a skull 50 and a guide member 506 coupled to the bolt 504. The bolt 504 may be substantially similar to the bolt 104 including a channel 524 extending therethrough along a longitudinal axis 5L. The guide member 506 is configured to lockingly engage the bolt 504 at any angle selected within a range of permitted angulation allowing the user to select an angle at which the longitudinal axis 5L' of the guide member 506 extends relative to the longitudinal axis 5L. Specifically, the guide member 506 and the bolt 504 include complementary projections which engage one another in a manner similar to the projections on variable angle locking screws and variable angle locking holes. Thus a catheter 514 may be inserted through a guide channel 508 of the guide member 506 fixed relative to the bolt to ensure the guide member extends along a user selected angle with respect to the bolt 504.

An inner surface forming the channel 524 includes a plurality of columns 526 extending along a length thereof, each of the plurality of columns 526 separated from one another via recessed portions 530. Each of the columns 526 includes a plurality of protrusions 528 for engaging corresponding threading on the guide member 506. The protrusions 528 may be, for example, spikes, pegs, projections or threads. The columns 526 may be similar to the channel 124 of the system 100, including a proximal portion which tapers radially inward from a proximal end thereof to a distal end thereof and a distal portion which flares radially outward from a proximal end thereof to a distal end thereof. Alternatively, the columns 526 may be curved outward toward a center of the channel 524. In another alternate embodiment, the columns 526, if connected across the recessed portions 530 may be partially hemispherical. The channel 524 may be substantially similar to a variable angle hole, as described in, for example, U.S. Patent Appln. Publication No. 2006/0235400, the entire disclosure of which is incorporated herein by reference.

The guide member 506 extends from a proximal end 548 to a rounded distal end 550 including threading 554 extending therearound. The user may determine a desired angulation of the guide member 506 and insert the distal end 550 into the channel 524 such that the threading 554 of the distal end 550 engages the protrusions 528 of the columns 526, fixing the guide member 506 therein at the desired angle. Once the guide member 506 has been fixed within the channel 524 at the desired angle relative to the longitudinal axis 5L, the catheter may be inserted through the guide channel 508. The system 500 may further include a compressible sealing plug 588 which is positioned about the catheter 514 and inserted into the proximal end 548 of the guide member 506 to seal the guide member 506 and fix the catheter 514 relative thereto. The compressible sealing plug 588 may be formed of, for example, silicone.

Although the exemplary embodiment specifically show and describe the channel 524 of the bolt 504 including a plurality of columns 526 for accommodating the guide member 506 at a variable angle, it will be understood by those of skill in the art that the bolt 504 may include any of a variety of structures for receiving the guide member 506 at a variable angle relative thereto. For example, the channel 524 may taper from a proximal end to a distal end to receive a corresponding enlarged portion of the guide member 506 at an angle with respect to the longitudinal axis 2L of the bolt 504, substantially as described in, for example, U.S. Pat. No. 6,893,443, the entire disclosure of which is incorporated herein by reference. In another example, a bushing including a sidewall with a slot may be rotatably inserted into the channel 524 of the bolt 504 such that when the guide member 506 is received through a bore of the bushing, the slot along the sidewall permits the bushing to expand and engage the inner surface of the channel. Thus, the guide member 506 is fixed therein at an angle relative to the longitudinal axis 2L, substantially as described in, for example, U.S. Pat. No. 6,235,033, the entire disclosure of which is incorporated herein by reference. In an alternate embodiment, a bushing is pivotally adjustable within the channel 524 such that the guide member 506 may be received therein at an angle relative to the longitudinal axis 2L, substantially as described in U.S. Pat. No. 7,682,379, the entire disclosure of which is incorporated herein by reference. In another example, a multi-axial pivotable insert (e.g., a helical insert) may be inserted into the channel of the bolt 504 such that the insert is rotationally fixed relative to the bolt 504 but is pivotally adjustable such that the guide member 506 may be received therein at an angle relative to the longitudinal axis 2L of the bolt 504, substantially as described in, for example, U.S.

Patent Application Pub. No. 2006/058797, the entire disclosure of which is incorporated herein by reference.

In yet another example, the channel 524 includes a geometry corresponding to the geometry along an exterior portion of the guide member 506 permitting the guide member 506 to be received therein at an angle with respect to the longitudinal axis 2L of the bolt 504 similarly to variable angle holes of bone plates as taught by Smith & Nephew®, Stryker®, Medartis®, Small Bone Innovations®, Biomet® and Anglefix®. In other examples, the channel 524 may be fit with integrated rings as taught by Stryker®, be configured to receive a polyaxial bushing as taught by Arthrex® and Depuy Orthopedics®, or be configured to receive rotatable bearings as taught by TriMed®. Although specific examples have been described above, it will be understood by those of skill in the art that the channel 524 of the bolt 504 and/or an exterior of the guide member 506 may include any of a variety of structures to facilitate insertion of the guide member 506 at an angle with respect to the longitudinal axis 2L of the bolt 504.

Figure 20:
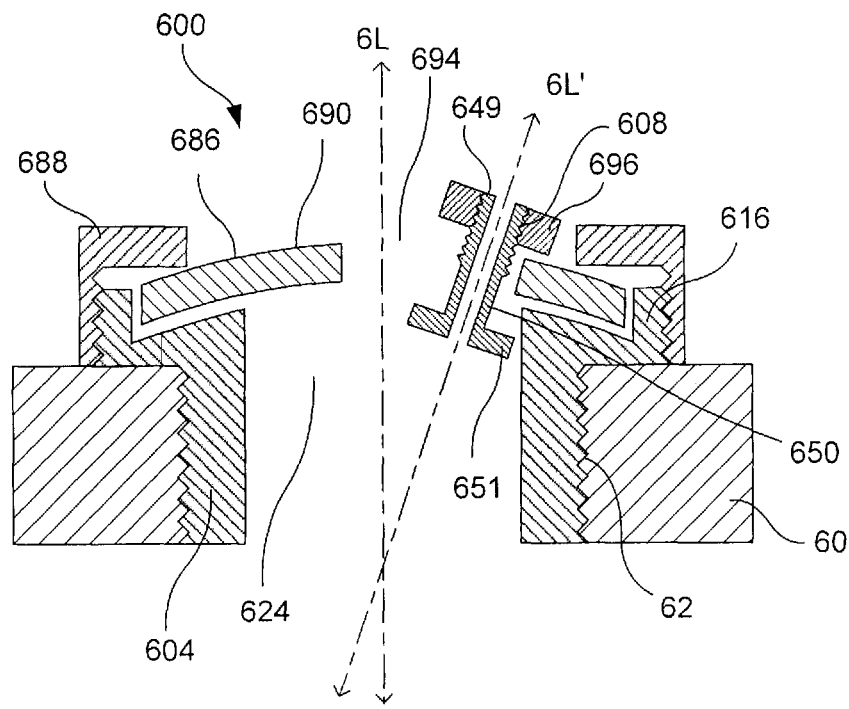
FIG. 20 shows a cross-sectional side view of a system according to a sixth exemplary embodiment of the present invention.
Figure 21:
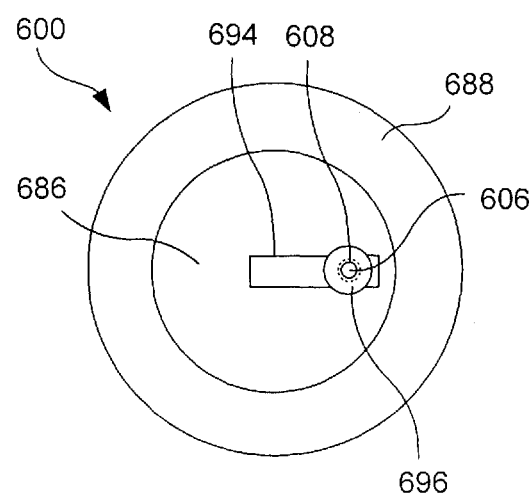
FIG. 21 shows a top plan view of the system of FIG. 20.

As shown in FIGS. 20-21, a system 600 according to a sixth exemplary embodiment of the present invention comprises a bolt 604 for engaging a hole 62 drilled in a skull 60, a slotted disc 686 placed within a cavity of a head portion 616 of the bolt 604 and fixed thereto via a first compression screw 688 and a guide member 606 received within a slot 694 of the disc 686 and held therewithin via a second compression screw 696. In a first configuration, the first compression screw 688 merely holds the disc 686 within the head 616 so that the disc 686 is rotatable therewithin and the second compression screw 696 permits the guide member 606 to be slid along the slot 694. In a second configuration the first and second compression screws 688, 696 are tightened over the head portion 616 and guide member 606, respectively, such that the disc 686 and the guide member 606 are both fixed relative to the bolt 604. The bolt 604 is substantially similar to the bolt 104 except as described below and includes a channel 624 extending therethrough along a longitudinal axis 6L thereof. The first compression screw 688 engages a threading along an outer surface of the head portion 616 to hold the disc 686 therewithin. The disc 686 may be curved such that a proximal surface 690 thereof is convex and is mounted to the head portion 616 of the bolt 604. As shown in FIG. 17, the slot 694 may extend through the disc 686 from approximately a center of the disc 686 proximate to an edge thereof.

The guide member 606 extends from a proximal end 648 to a distal end 650 along a longitudinal axis 6L' and includes a guide channel 608 extending therealong for receiving a catheter therethrough. The guide member 606 is sized and shaped to be received within the slot 694 of the disc 686 and slidable therein. The proximal end 648 includes threading 649 therealong for engaging the second compression screw 696. The second compression screw 696 prevents the guide member 606 from falling distally through the slot 694. The distal end 650 of the guide member 606 may include a shoulder 651 extending radially outward to prevent the guide member 606 from being inadvertently pulled proximally through the slot 694. In the first configuration, the guide member 606 may be slid along the slot 694 and the disc 686 rotated about the longitudinal axis 6L until the longitudinal axis 6L' of the guide member 606 at a desired angle and orientation relative to the longitudinal axis 6L of the bolt 604. It will be understood by those of skill in the art that rotating the disc 686 and sliding the guide member 606 within the slot 694 permits the longitudinal axis 6L' to be moved in a variety of different orientations and angles with respect to the longitudinal axis 6L of the bolt 604. Once the desired position and angulation of the guide member 606 relative to the bolt 604 have been achieved, the first and second compression screws 688, 696 are moved to the second configuration to fix the disc 686 and the guide member 606, respectively, relative to the bolt 604. The first compression screw 688 is tightened over the head portion 616 of the bolt 604 to fix the disc 686 in the desired position and prevent the disc 686 from rotating relative thereto. The second compression screw 696 is tightened over the proximal end 648 of the guide member 606 (i.e., moved distally therealong) until both the shoulder 651 and the second compression screw 696 contact the disc 686, thereby locking the guide member 606 in the desired position and angulation relative to the disc 686 and the bolt 604.

Figure 22:
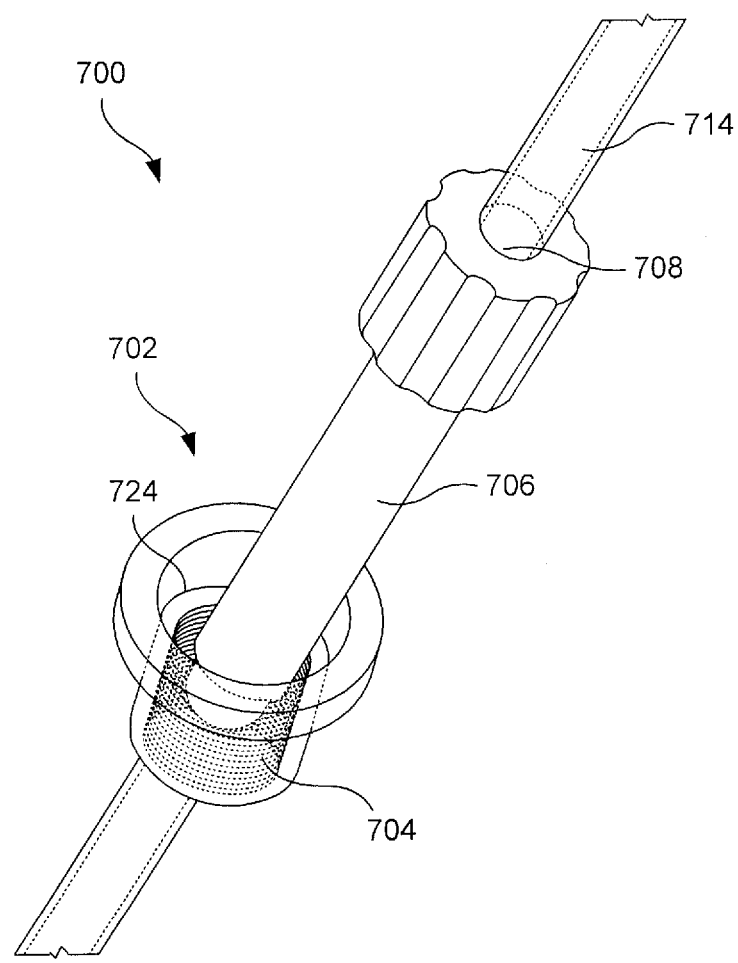
FIG. 22 shows a perspective view of a system according to a seventh exemplary embodiment of the present invention.

As shown in FIGS. 22-23, a system 700 according to a seventh exemplary embodiment of the present invention is substantially similar to the system 100 except as described below, comprising a catheter guiding device 702 including a bolt 704 for engaging a hole drilled in a skull and a guide member 706 movably couplable thereto such that a catheter 714 may be inserted through the hole drilled in the skull via a guide channel 708 of the guide member 706. The bolt 704 may be substantially similar to the bolt 104 including a channel 724 extending therethrough along a longitudinal axis 7L. The channel 724, however, includes a membrane 740 extending radially inward from a portion thereof and a rim 742 extending along a radially inner edge thereof. A circumference formed via the rim 742 is sized and shaped to receive a distal end 750 of the guide member 706 therein. The membrane 740 may plastically deform as the guide member 706 is moved relative to the bolt 704.

The guide member 706 may be substantially similar to the guide member 106, extending along a longitudinal axis 7L' from a proximal end 748 to a distal end 750, the guide channel 708 extending therethrough along the longitudinal axis 7L'. The distal end 750 may have a smaller diameter than a remaining length thereof such that when the distal end 750 is inserted into the channel 724, the distal end 750 engages the rim 742 of the membrane 740 and the remaining length of the guide member 706 is prevented from moving distally therepast. The guide member 706 may be moved relative to the bolt 704 such that the longitudinal axis 7L' of the guide member 706 may be angled with respect to the longitudinal axis 7L. The membrane 740 is plastically deformed to accommodate the angling and movement of the guide member 706 relative to the bolt 704. Once the guide member 706 has been moved to a desired orientation and angle with respect to the longitudinal axis 7L of the bolt 704, the catheter 714 may be inserted through the guide channel 708. A compressible seal formed of, for example, silicone, may be placed within a proximal opening 726 of the channel 724 surrounding the guide member 706 to fix the guide member in the desired position relative to the bolt 704. In another embodiment, the guide member 706 may be removed once the catheter 714 has been inserted therethrough, and the compressible seal inserted into the proximal opening 726 surrounding the catheter 714 to fix the catheter 714 in the desired position relative to the bolt 704.

Figure 24:
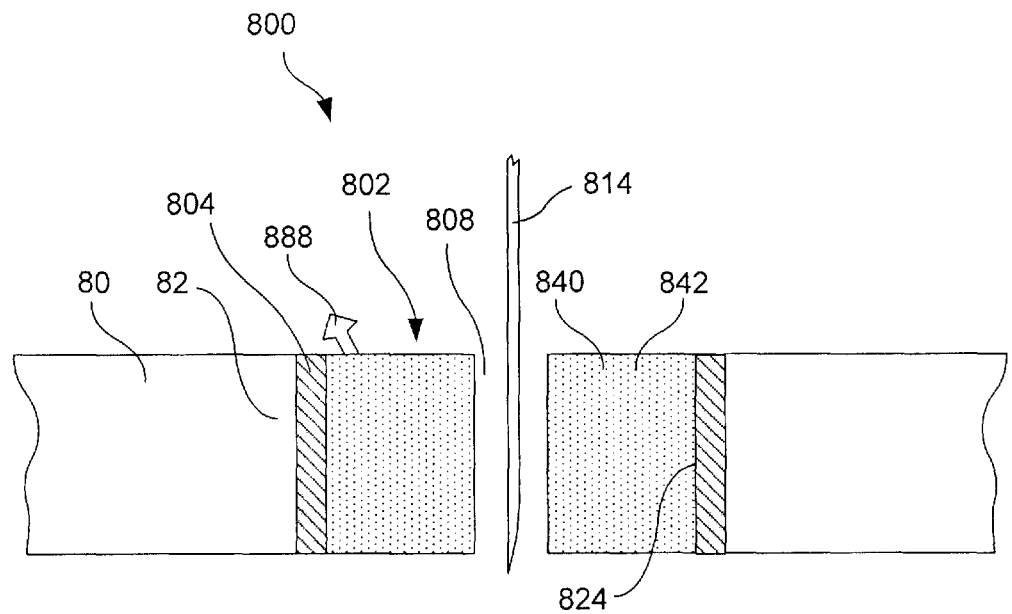
FIG. 24 shows a cross-sectional side view of a system according to an eighth exemplary embodiment of the present invention, in a first configuration.
Figure 25:
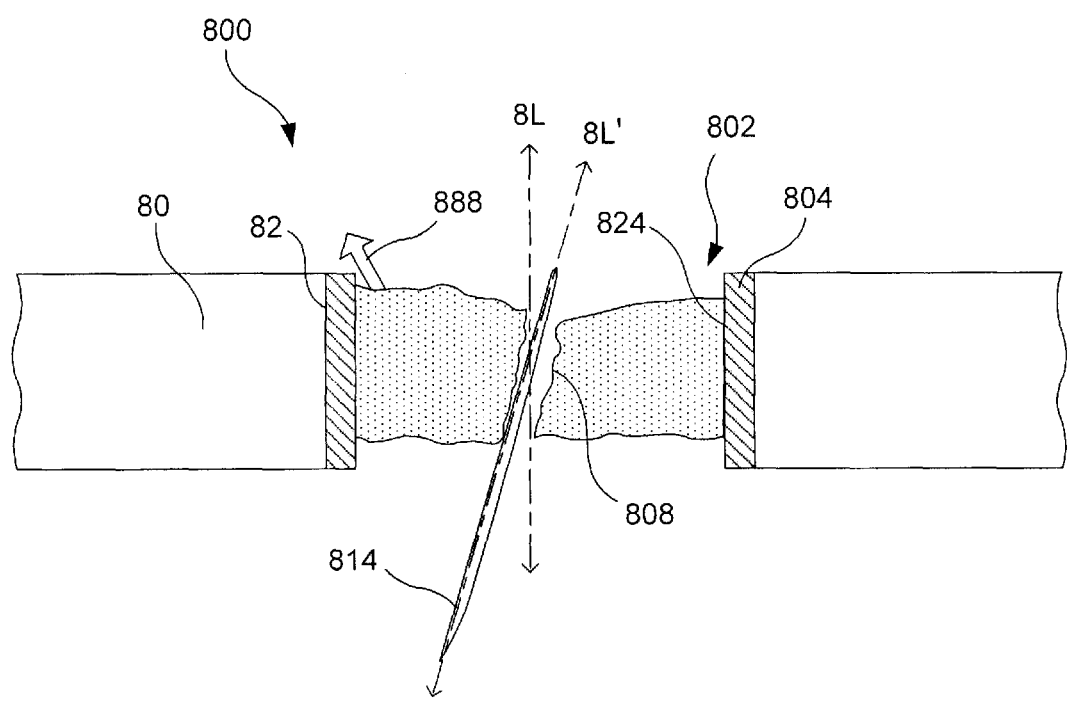
FIG. 25 shows a cross-sectional side view of the system of FIG. 24, in a second configuration.

As shown in FIGS. 24-25, a system 800 according to an eighth exemplary embodiment of the present invention is substantially similar to the system 100 except as described below, comprising a catheter guiding device 802 including a bolt 804 for engaging a hole 82 drilled in a skull 80 and a catheter 814 couplable to the bolt 804 in a desired angulation/orientation relative thereto. In an alternative embodiment, a guide member may be coupled to the bolt 804 in a desired angulation/orientation relative thereto and the catheter 814 inserted therethrough. The bolt 804 may be substantially similar to the bolt 104, a channel 824 extending through the bolt 804 along a longitudinal axis 8L thereof. An inner surface of the channel 824, however, is padded with a cushion 840 including a channel 808 extending therethrough, which is sized and shaped to receive the catheter 814 therein. The cushion 840 may be filled with a material 842 which transforms the cushion 840 from an insertion configuration, as shown in FIG. 24, in which the catheter 814 may be inserted through the channel 808 to a locked configuration, as shown in FIG. 25, in which the catheter 814 is locked at a desired position relative to the bolt 804.

In the insertion configuration, the catheter 814 may be inserted through the channel 808 and moved relative to the bolt 804 until a longitudinal axis 8L' of the catheter is at a desired angle and orientation relative to the longitudinal axis 8L of the bolt 804. Once the catheter 814 has been moved to the desired angulation/orientation relative to the bolt 804, the cushion 840 may be transformed to the locked configuration. In one exemplary embodiment, the material 842 in the cushion 840 may be a liquid with hardening properties such as, for example, light-curable resin. When the cushion 840 is in the insertion configuration, the filling material 842 is in the liquid state and when the cushion 840 is in the locked configuration the filling material 842 has been transformed to the hardened state. In another embodiment, the cushion 840 may be filled with air via, for example, a valve 888 included thereon, to transform the cushion 840 from the insertion configuration to the locked configuration. In yet another embodiment, the material 842 filling the cushion 840 may be granules and air such that the granules are movable relative to one another in the insertion configuration. When a vacuum pressure is applied to remove the air from the cushion 840, only the granules remain such that the cushion 840 becomes stiff, fixing the catheter 814 therein in the desired position relative to the bolt 804. The granules may be, for example, sand, ceramic, etc. In some cases, additional fixation may be necessary. In these cases, a compressible seal (e.g., a silicone nut) may be inserted through the proximal opening of the channel 824 to provide additional sealing and fixation of the guide member 806 relative to the bolt 804.

It will be apparent to those skilled in the art that various modifications and variations can be made in the structure and the methodology of the present invention, without departing from the spirit or the scope of the invention. Thus, it is intended that the present invention cover the modifications and the variations of this invention provided that they come within the scope of the appended claims and their equivalents.

What is claimed is:

1. A catheter guiding device, comprising:
a bolt including a shaft configured to be inserted within a hole drilled in a bone and a passageway extending longitudinally therethrough along a bolt axis;
a guide member received within the passageway of the bolt and extending longitudinally along a guide axis, the guide member including a guide channel extending therethrough along the guide axis, wherein, in a first configuration, the guide member is movable relative to the bolt within a predetermined range of angulation to alter an angle between the guide axis and the bolt axis to a desired angle aligning the guide axis with a target area and, in a second configuration, the guide member is fixed in the desired angle; and
a coupling element coupling the guide member to the bolt, the coupling element movably received within the passageway and receiving a distal portion of the guide member therein,
wherein the coupling element is a slotted bushing, the distal portion of the guide member received within the bushing along a central axis thereof such that the guide axis and the central axis are substantially coaxial,
wherein the slotted bushing is movable relative to the bolt in a first configuration and locked relative to the bolt in a second configuration, and
wherein, in the first configuration, the slotted bushing is biased in a non-expanded configuration and, in the second configuration, the slotted bushing is in an expanded configuration such that the central axis of the bushing is fixed at the desired angle with respect to the bolt.

2. The device according to claim 1, wherein the shaft of the bolt includes a threading therealong to engage the hole drilled in the bone.

3. The device according to claim 1, wherein the bolt includes a head portion at a proximal end thereof sized and shaped to be engaged by a driving tool.

4. The device according to claim 1, wherein the passageway of the bolt includes a proximal portion which tapers radially inward from a proximal end thereof towards a distal end thereof and a distal portion which flares radially outward from a proximal end thereof toward a distal end thereof to accommodate the guide member within the permitted range of angulations.

5. The device according to claim 1, wherein the slotted bushing includes a threaded inner surface tapering from a proximal end to a distal end and a distal portion of the guide member includes a correspondingly threaded exterior surface tapering to the distal end thereof, the guide member being rotatable relative to the bushing to move the bushing between the non-expanded and the expanded configuration.

6. The device according to claim 1, wherein an outer surface of the bushing is at least partially spherical and is received within a correspondingly spherically shaped portion of the passageway such that the bushing is movable with respect to the bolt.

7. The device according to claim 1, wherein an outer surface of the bushing includes a protrusion extending therefrom and received within a corresponding recess of the passageway such that the bushing is prevented from rotating with respect to the bolt.

8. The device according to claim 1, wherein the bolt includes a plurality of probe channels extending therethrough circumferentially about the passageway, the channels sized and shaped to receive a probe therethrough.

9. The device according to claim 8, wherein the probe channels are spaced equidistantly from one another.

10. The device according to claim 8, wherein the probe channels extend along probe axes which are angled with respect to the bolt axis such that the probe channels are prevented from intersecting with the guide axis at the desired angle.

11. The device according to claim 1, wherein the passageway includes a locking structure engagable with a corresponding structure of the guide member to fix the guide member therein at the desired position.

12. The device according to claim 1, wherein the guide channel is sized and shaped to receive a catheter therethrough.

13. The device according to claim 1, wherein the guide member is a catheter.

14. The device of claim 1, wherein the bushing lockingly receives the distal end of the guide member so that the guide member opens into the passageway of the bolt.

15. The device of claim 14, wherein the passageway of the bolt includes a shoulder extending radially thereinto to prevent the bushing from moving distally past a desired location in the passageway, thereby preventing the guide member from moving distally past the desired location in the passageway.

16. A system for draining cerebrospinal fluid, comprising:
a bolt including a shaft configured to be inserted within a hole drilled in a bone and a passageway extending longitudinally therethrough along a bolt axis;
a guide member received within the passageway of the bolt and extending longitudinally along a guide axis, the guide member including a guide channel extending therethrough along the guide axis, wherein, in a first configuration, the guide member is movable relative to the bolt within a predetermined range of angulation to alter an angle between the guide axis and the bolt axis to a desired angle aligning the guide axis with a target area and, in a second configuration, the guide member is fixed in the desired angle;
a catheter insertable through the guide channel to the target area; and
a coupling element coupling the guide member to the bolt, the coupling element movably received within the passageway and receiving a distal portion of the guide member therein,
wherein the coupling element is a slotted bushing, the distal portion of the guide member received within the bushing along a central axis thereof such that the guide axis and the central axis are substantially coaxial,
wherein the slotted bushing is movable relative to the bolt in a first configuration and locked relative to the bolt in a second configuration, and
wherein, in the first configuration, the slotted bushing is biased in a non-expanded configuration and, in the second configuration, the slotted bushing is in an expanded configuration such that the central axis of the bushing is fixed at the desired angle with respect to the bolt.

17. The system according to claim 16, further comprising:
a guiding tool including a base and a plurality of legs extending therefrom, the base including an opening extending therethrough so that when the guiding tool is slid along a length of the guide member such that the legs abut the bone, a central axis of the opening is one of substantially perpendicular to a surface of the bone and coaxial with the bolt axis.

18. The system according to claim 17, wherein the base of the guiding tool includes a recess extending through a portion thereof, the recess sized and shaped to engage a proximal end of the bolt such that rotation of the guiding tool correspondingly rotates the bolt to engage the hole in the bone.

19. The system according to claim 16, further comprising a driving tool sized and shaped to engage a proximal end of the guide member such that rotation of the driving tool correspondingly rotates the guide member relative to the bolt.

20. A guiding device, comprising:
a guide member configured to be inserted within a hole drilled in a bone, the guide member extending longitudinally along a guide axis and including a guide channel extending therethrough along the guide axis, wherein, in a first configuration, the guide member is movable relative to a bolt within a predetermined range of angulation to alter an angle between the guide axis and the bolt axis to a desired angle aligning the guide axis with a target area and, in a second configuration, the guide member is fixed in a desired angle; and
a cap including an opening extending therethrough slidable over a proximal end of the guide member to fix the guide member in the second configuration,
wherein the guide member is coupled to the bolt with a coupling element, the coupling element movably received within a passageway of the bolt and receiving a distal portion of the guide member therein,
wherein the coupling element is a slotted bushing, the distal portion of the guide member received within the bushing along a central axis thereof such that the guide axis and the central axis are substantially coaxial,
wherein the slotted bushing is movable relative to the bolt in a first configuration and locked relative to the bolt in a second configuration, and
wherein, in the first configuration, the slotted bushing is biased in a non-expanded configuration and, in the second configuration, the slotted bushing is in an expanded configuration such that the central axis of the bushing is fixed at the desired angle with respect to the bolt.

21. The device according to claim 20, wherein the guide member is a catheter.

22. The device according to claim 20, further comprising a fixation element fixing the cap to the bolt.

* * * * *